United States Patent [19]
Bertocchio et al.

[11] Patent Number: 5,892,137
[45] Date of Patent: Apr. 6, 1999

[54] PURIFICATION OF PENTAFLUROETHANE

[75] Inventors: Rene Bertocchio, Vourles par Vernaison; Andre Lantz, Vernaison, both of France

[73] Assignee: Elf Atochem S.A., France

[21] Appl. No.: 943,182

[22] Filed: Oct. 3, 1997

[30] Foreign Application Priority Data

Oct. 18, 1996 [FR] France ................................... 96 12714

[51] Int. Cl.⁶ .................................................... C07C 17/38
[52] U.S. Cl. ............................................................ 570/179
[58] Field of Search .............................................. 570/179

[56] References Cited

U.S. PATENT DOCUMENTS 3,755,477  8/1973  Firth et al. .
4,950,816  8/1990  Tung et al. .............................. 570/179
5,585,529  12/1996  Corbin et al. ........................... 570/179

FOREIGN PATENT DOCUMENTS

| | | |
|---|---|---|
| 0389334 | 9/1990 | European Pat. Off. ................ 570/179 |
| 456 552 A1 | 4/1991 | European Pat. Off. . |
| 506 525 | 3/1992 | European Pat. Off. . |
| 456 552 B1 | 1/1994 | European Pat. Off. . |
| WO 94 122793 | 10/1994 | WIPO . |

*Primary Examiner*—Alan Siegel
*Attorney, Agent, or Firm*—Bell, Boyd & Lloyd

[57] ABSTRACT

To remove the traces of chlorotrifluoroethylene (F1113) which are present in a pentafluoroethane (F125), the F125 is passed through a bed of active carbon.

9 Claims, No Drawings

PURIFICATION OF PENTAFLUROETHANE

FIELD OF THE INVENTION

The present invention relates to the field of hydrofluoroalkanes (HFA) and its subject-matter is more particularly the purification of pentafluoroethane containing chlorotrifluoroethylene.

BACKGROUND OF THE INVENTION

Pentafluoroethane (known in the trade under the designation F125) has been proposed as a substitute for chloropentafluoroethane (F115) and for chlorodifluoromethane (F22) for the applications linked with the refrigeration industries; on its own or in combination with other HFAs it is especially advantageous for replacing the refrigerant R502 (azeotropic mixture of F115 and F22) widely employed hitherto for the production of industrial cooling.

F125 can be obtained by hydrogenolysis of F115, as described in patent EP 506 525, or by liquid- or gas-phase fluorination of chlorinated or chlorofluorinated compounds. Among these processes there may be mentioned more particularly those starting from olefins like perchloroethylene with addition of a first molecule of HF and substitution of the other chlorine atoms as described in U.S. Pat. No. 3,755,477; as indicated in patent EP 456 552 it is also possible to start with intermediate fluorination products such as 1,1,1-trifluorodichloroethane (F123) and 1,1,1,2-tetrafluorochloroethane (F124).

These processes, in particular those using elevated temperatures, give rise to olefins which are well known for their toxicity as well as for their reactivity. Even at relatively low concentrations these olefins can, for example, be oxidized in contact with air and result in acidic conversion products making the F125 unsuitable for its commercialization.

After distillation, pentafluoroethane can still contain chlorotrifluoroethylene (F1113) originating from the dechlorohydration of 1,2-dichloro-1,1,2-trifluoroethane (F123a), a normal byproduct of the fluorination of perchloroethylene, or from the dehydrofluorination of chlorotetrafluoroethanes (F124 and F124a). During prolonged storage of F125 and in the presence of traces of air which are normally dissolved in liquid F125, F1113 can be easily oxidized and, in contact with residual moisture, result in the formation of acidic products such as HCl, HF and $CF_3COOH$. Furthermore, besides its sensitivity to oxidation, F1113 is well known for its ability to polymerize or copolymerize in the presence of other olefins.

DESCRIPTION OF THE INVENTION

It has now been found that the residual F1113 in an F125 can be removed by passing the F125, in gas or liquid phase, through a bed of active carbon and that F1113 can subsequently be desorbed without loss of efficiency and capacity of the adsorbent.

The subject-matter of the invention is therefore a process for the purification of an F125 containing F1113, characterized in that a stream of the F125 to be purified is passed through a bed of active carbon.

The active carbon to be employed may be chosen from carbons of high specific surface (generally between 800 and 1500 $m^2/g$). Since the percentage of microporosity is, by definition, the surface fraction corresponding to the pores of diameter smaller than or equal to 2 nm, an active carbon which has a microporosity of the order of 50 to 90%, preferably 70 to 85%, is advantageously employed. These active carbons can be employed as they are after drying at 135°–145° C. and, after use, they can be regenerated at reduced pressure at a temperature of at least 200° C. or by purging under a stream of inert gas such as nitrogen or helium to a final temperature of approximately 250° C. In this case the application of temperature is preferably made gradually and in steps starting from 100° C. in order to avoid any conversion of the F1113 on the adsorbent.

The process according to the invention can be applied to the purification of an F125 containing up to 10 000 ppm of F1113, preferably from 10 to 1000 ppm, as well as variable quantities of saturated impurities like F124.

The treatment according to the invention can be performed in gas phase or in liquid phase at a temperature of between −20° and +80° C., preferably between 10° and 40° C. and at a pressure ranging from 100 to 2200 kPa.

For the treatment in gas phase a flow rate is employed corresponding to a space velocity of between 50 and 1500 v/h/v (volume of F125/hour/apparent volume of adsorbent) with a flow velocity of 10 to 2500 cm/min. In liquid phase these velocities are reduced to 4–20 v/h/v and 5–40 cm/minute respectively.

EXAMPLES

The following examples illustrate the invention without limiting it. The ppm values shown are expressed by weight.

Example 1

A charge of 36 g of CECA AC 35 activated carbon as 3-mm granules was placed in a stainless steel tube 50 cm in height and 30 mm in internal diameter comprising a metal grid at one third of its height, and then a gas stream of crude F125 containing 17 ppm of F1113 and 970 ppm of F115 was passed through it at ambient temperature and at a flow rate of 10 l/h.

After two hours' operation no trace of F1113 (<1 ppm) was detected at the exit of the purifier and only 350 ppm of F115.

After 4 hours the removal of F1113 was still quantitative but the concentration of F115 had returned to its initial value.

The carbon CECA AC 35 has an apparent density of 0.45 g/ml, a specific surface of 1335 $m^2/g$ and a microporosity of 78%.

Example 2

In the same apparatus as that employed in Example 1 was placed a charge of 34 g of Norit RDBX 1.5 activated carbon over which was then passed, at ambient temperature and at a flow rate of 4 l/h, a gas stream of crude F125 containing 245 ppm of F1113 and 2.4% of F124.

The breakthrough point for the F1113 appeared in these conditions after 31 hours' running, which corresponds to a capacity of 0.5 g of F1113 retained per 100 g of dry carbon.

Norit RDBX 1.5 has an apparent density of 0.443 g/ml and a specific surface of 1358 $m^2/g$ at a microporosity content (pore diameter $\leq 2$ nm) of 85%.

Example 3

A charge of 33.4 g (75 ml) of CECA GAC 1240 Plus active carbon was placed in a stainless steel tube 50 cm in height and 30 mm in internal diameter, and then a gas stream of crude F125 containing 305 ppm of F1113, 1050 ppm of F115, 71 ppm of F124, 24 ppm of F23 and 39 ppm of F143a was passed through it at ambient temperature and at a flow rate of 4 l/h.

After passing over the carbon bed, F1113 and F124 were completely removed. F124 reappeared only after 16 hours' running and F1113 after 41 hours (residual concentration >1 ppm). At this point the retention capacity of the carbon for F1113 was 0.74%.

The carbon charge was then removed from the purifier and heated for 2 hours at 200° C. at reduced pressure (0.1 kPa) and then replaced in order to pass the same stream of crude F125 through it again. During this new adsorption cycle the same total removal of F124 and of F1113 was noted, the breakthrough point for the latter appearing only after 37 hours, which corresponds to an adsorption capacity of 0.73%.

This example shows that the active carbon is completely regenerable after an adsorption cycle and that it retains all its efficiency and its capacity.

The carbon GAC 1240 (CECA) has an apparent density of 0.443 g/ml, a specific surface of 1284 m$^2$/g and a microporosity content (pores of diameter $\leq$2 nm) of 72%.

Example 4

432 g of crude F125 containing 300 ppm of F1113 were passed, at a flow rate of 17.3 l/h, through a bed of GAC 1240 Plus active carbon as 0.5–1.5-mm particles; the purifier tube with an internal diameter of 8 mm and a working height of 35 cm contained 7.6 g of active carbon.

A sample of the treated F125 taken at the exit of the purifier after 100 minutes' operation contained no detectable trace of F1113 (<1 ppm), which confirms the efficiency of the process at high running rates.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Process for the purification of a pentafluoroethane (F125) containing chlorotrifluoroethylene (F1113), comprising:

passing a stream of F125 containing F1113 in gas or liquid phase through a bed of active carbon for adsorbing the F1113 thereon, said active carbon having a specific surface of between 800 and 1500 m$^2$/g and a microporosity of 50 to 90%, and wherein the process is carried out at a temperature of between $-20°$ and $+80°$ C., and at a pressure ranging from 100 to 2200 kPa,; and regenerating the bed of active carbon to desorb the F1113.

2. The process of claim 1 wherein the bed of active carbon is regenerated by removing the stream of F125 containing F1113 from the bed of active carbon, and heating the bed of active carbon at a temperature of at least 200° C.

3. The process of claim 2 wherein the bed of active carbon is regenerated by purging under a stream of inert gas to a final temperature of about 250° C.

4. The process of claim 2 wherein the bed of active carbon is regenerated by gradually increasing the applied heat beginning at about 100° C. to avoid conversion of the F1113 on the bed of active carbon.

5. The process of claim 1 wherein the stream contains up to 10,000 ppm of F1113.

6. The process of claim 1 wherein the stream contains 10 to 1,000 ppm of F1113.

7. The process of claim 1 wherein the process is carried out at between 10° and 40° C., and wherein the active carbon has a microporosity of 70 to 85%.

8. The process according to claim 1 wherein the process is carried out in gas phase with a flow rate of F125 to be purified corresponding to a space velocity of between 50 and 1500 v/h/v, with a flow velocity of 10 to 2500 cm/min.

9. The process according to claim 1 wherein the process is carried out in liquid phase with a flow rate of F125 to be purified corresponding to a space velocity of between 4 and 20 v/h/v, with a flow velocity of 5 to 40 cm/min.

* * * * *